(12) United States Patent
Lavie

(10) Patent No.: US 7,122,518 B2
(45) Date of Patent: Oct. 17, 2006

(54) METHOD FOR PREVENTING OR REDUCING COLLATERAL PHOTOTOXIC DAMAGE TO NEIGHBORING TISSUES DURING PHOTODYNAMIC THERAPY OF A TARGET TISSUE

(75) Inventor: Gad Lavie, Rehovot (IL)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/720,688

(22) Filed: Nov. 25, 2003

(65) Prior Publication Data

US 2004/0176345 A1 Sep. 9, 2004

Related U.S. Application Data

(60) Provisional application No. 60/428,677, filed on Nov. 25, 2002.

(51) Int. Cl.
*A61K 31/195* (2006.01)

(52) U.S. Cl. .............. 514/5.61; 514/569; 514/680; 514/912

(58) Field of Classification Search ............ 514/185, 514/561, 569, 680, 912
See application file for complete search history.

(56) References Cited

U.S. PATENT DOCUMENTS

| | | | |
|---|---|---|---|
| 5,047,435 A | 9/1991 | Lavie et al. | |
| 6,087,141 A * | 7/2000 | Margolis-Nunno et al. | 435/173.3 |

OTHER PUBLICATIONS

Medline Abstract 10755329, Scott et al., 2000.*

* cited by examiner

*Primary Examiner*—Zohreh Fay
(74) *Attorney, Agent, or Firm*—Browdy and Neimark, PLLC

(57) ABSTRACT

A method is provided for preventing or reducing the adverse effects of photodynamic therapy such as collateral damage by regulating the localized phototoxicity of an effector photosensitizer molecule. During photodynamic therapy, the activity of the effector photosensitizer molecule in neighboring tissues of the tissue targeted for destruction is quenched by a quenching photosensitizer molecule.

19 Claims, 8 Drawing Sheets

METHOD FOR PREVENTING OR REDUCING COLLATERAL PHOTOTOXIC DAMAGE TO NEIGHBORING TISSUES DURING PHOTODYNAMIC THERAPY OF A TARGET TISSUE

CROSS-REFERENCE TO RELATED APPLICATIONS

This application claims the benefit of priority from provisional U.S. application No. 60/428,677, filed Nov. 25, 2002, the entire content of which is herein incorporated by reference.

BACKGROUND OF THE INVENTION

1. Field of the Invention

The present invention relates to photodynamic therapy and a method for preventing or reducing adverse effects during photodynamic therapy. In particular, the present invention relates to photodynamic therapy for age-related macular degeneration and tumors.

2. Description of the Related Art

Photodynamic therapy (PDT) is a treatment modality that is gradually entering clinical medicine. PDT is used to treat light-accessible localized tumors at sites where avoiding deforming surgery is a priority (McCaughan, 1984; Dougherty, 1984). PDT is also used in ophthalmology where it is an accepted treatment modality for causing occlusion of pathological microvessels emerging from the retinal choroid in the neovascular form of age related macular degeneration (Brown et al., 2001; Schmidt-Erfurth et al., 1999).

Age related macular degeneration (AMD) is a manifestation that occurs in elderly people, in which choroidal neovascularization (development of pathological blood vessels emerging from the choroid) is the major cause of blindness due to damage to the retinal pigmented epithelium and to the optic nerve (McLeod et al., 2000). These abnormal blood vessels cause apoptosis of the retinal pigmented epithelial (RPE) cells and consequently degeneration of neural retina photoreceptor cells. Since AMD is the primary cause of blindness in the elderly and constitutes a major cause of suffering and diminished quality of life, major efforts are directed to the treatment of AMD.

Current approaches to contain this problem have thus far focused on destroying these blood vessels by photodynamic therapy. The pathological vessel is photosensitized and irradiated with a concerted beam of laser light at wavelengths absorbed by the photosensitizer, i.e., argon laser at 689 nm with verteporfin as the photosensitizer. Reactive oxygen species such as singlet oxygen and free radicals are generated in this process and induce photodynamic damage (phototoxicity) to the endothelial cell layers that line the blood vessel, leading to ultimate destruction of the pathological vessel.

The sole photosensitizer that is approved for clinical use in photodynamic therapy of AMD is a benzoporphyrin derivative verteporfin known by its trade name VISUDYNE. This compound is a lipophilic reagent that attaches to low density lipoprotein (LDL) in the plasma and enters cells via the LDL receptor system. It has a visible range absorption peak at 689 nm, and a laser source is used in photosensitization.

A major disadvantage to this treatment modality is attributed to the pharmacokinetic properties of verteporfin (VISUDYNE), where there is a strict time-related limitation. Following intravenous administration, VISUDYNE remains in the intravascular compartment for only 30 minutes after which time it begins to disperse in the tissues. In the eye, the compound extravasates to the adjacent retinal pigmented epithelium (RPE), an ultra thin layer consisting of only 10 layers of cells. Laser therapy administered when VISUDYNE has spread to the RPE results in damage to the RPE, apoptosis (self-induced programmed cell death) of these cells and irreversible blindness. Clinicians, therefore, have a limited time frame of 20 minutes to no more than 30 minutes after intravenous administration of VISUDYNE to complete the laser portion of the treatment. Even within this limited time frame, the pathological nature of the vessel can, in many cases, lead to premature or accelerated leakage of the compound to the adjacent RPE and the laser treatment can result in severe adverse effects, such as extensive injury to the thin layer of macular RPE and vision impairment (Michels et al., 2002). As a result, ophthalmologists remain uneasy about performing these photodynamic treatments, and even when done, only the minimal number of treatments are applied resulting in low suboptimal cure rates.

In the absence of any other satisfactory treatment for AMD, ophthalmologists have been looking for ways to improve the level of RPE protection from phototoxicity and prevent collateral damage. These efforts focused on generating elevated levels of antioxidants in the RPE to neutralize cytotoxic reactive oxygen species resulting from photosensitization (Ochsner et al., 1997). However, obtaining high protective antioxidant concentrations in the RPE that will be selective and not include the endothelium of the choroidal vasculature targeted for destruction has yet to be achieved.

Hypericin is an aromatic polycyclic dione (perihydroxylated naphthodianthrone; dianthraquinone) compound which has previously been found to possess photodynamic properties (Duran et al., 1986 and Giese, 1980). It is lipophilic and has visible range light absorption peaks at 545 and 589 nm. The chemical structure of hypericin is shown in FIG. 1A. In the presence of light (and possibly other sources of energy), this compound excites oxygen to its singlet state and is capable of generating superoxide radicals which can lead, among other things, to oxidation of tryptophan imidazole groups in proteins and oxidation of fatty acids in biological systems.

Hypericin exhibits numerous potent biological activities, some of which have been found to occur in complete darkness. While inhibition of protein kinase C (Takahashi et al., 1989) and inhibition of MAP kinase activation (Agostinis et al., 1995) have been reported to be light dependent, recent unpublished work from the laboratory of the present inventor indicates that MAP kinase activation can occur in complete darkness. The present inventor and his colleagues have also investigated the use of hypericin and its quinone-containing analogs in the inactivation of retroviruses. See, for example, U.S. Pat. No. 5,047,435; Degar et al. (1991); Lavie et al. (1989); Lavie et al. (1989); Lavie et al. (1990); Lavie et al. (1991); Meruelo et al. (1988); Meruelo et al. (1991); Valentine et al. (1989); and Weiner et al. (1989). Hypericin is now considered as a potentially effective antiviral drug which can be used against a number of diseases caused by viruses.

Furthermore, hypericin has been found to cause (A) inhibition of cytotoxic T cell mediated cytotoxicity (U.S. Pat. No. 5,514,714 diseases) and can be used to inhibit T cell mediated diseases such as psoriasis; (B) anticancer activities in vivo against highly metastatic murine breast adenocarcinoma and anaplastic squamous cell carcinoma (U.S. Pat. Nos. 6,001,882 and 6,229,048 B1), and (C) inhibition of angiogenesis induced with heparanase or FGF-2 in the rat eye pocket model (U.S. Pat. No. 6,229,048 B1).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for preventing or reducing the adverse effects of photodynamic therapy such as collateral damage. This method regulates the localized phototoxicity of an effector photosensitizer molecule during photodynamic therapy by quenching the activity of the effector photosensitizer molecule in neighboring tissues of the tissue targeted for destruction. Prior to administering the effector photosensitizer molecule and performing photodynamic therapy, a quenching photosensitizer molecule, the absorption spectrum of which falls outside the wavelength range used to excite the effector photosensitizer molecule, is administered to a patient to quench the activity of the effector photosensitizer molecule in tissues neighboring the target tissue during photodynamic therapy.

In particular, the present invention provides a method for preventing or reducing the adverse effects to retinal pigmented epithelium during photodynamic therapy of age related macular degeneration with an effector photosensitizer molecule.

BRIEF DESCRIPTION OF THE DRAWINGS

In FIGS. 2A and 2B, the cells were treated with hypericin for 3 hrs. and 6 hrs., respectively, and then exposed to 0.77 J/cm$^2$ of light irradiation. In FIGS. 2C and 2D, the cells were treated with hypericin for 3 hrs. and then exposed to either 0.96 J/cm$^2$ (FIG. 2C) or 1.73 J/cm$^2$ (FIG. 2D) of light irradiation.

FIG. 6A shows that 15 minutes after intravenous administration of hypericin to male Wistar rats, in the retina the compound is confined to the choroidal blood vessels. Two hrs after hypericin administration, the compound spreads to the entire retina (FIG. 6B), and after 6 hrs, hypericin is present only in the retina and not in the blood vessels (FIG. 6C). Arrows point to locations of blood vessels in cross-section.

DETAILED DESCRIPTION OF THE INVENTION

Figure 1A:
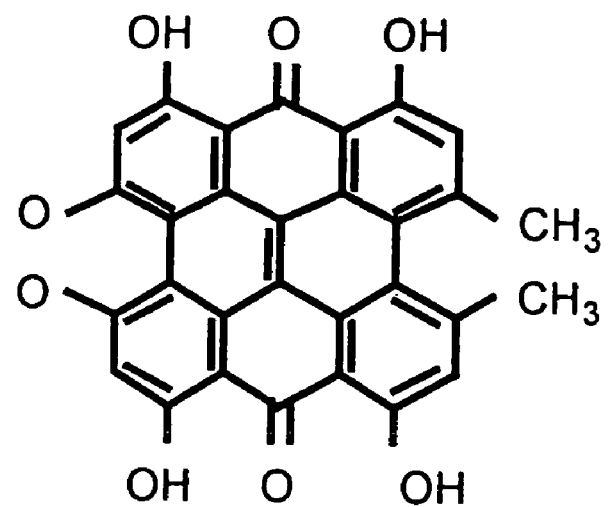
FIG. 1A shows the chemical structure of hypericin.

A novel concept termed "competitive quenching" employing a secondary photosensitizer to quench the photosensitizing activity of a primary sensitizer has been developed by the present inventor. The wavelength range of the laser beam used for primary photosensitizer excitation must fall outside the light absorption wavelength range of the quenching secondary photosensitizer. The present invention responds to a need to protect tissues adjacent to those targeted for destruction by photosensitization from collateral phototoxic damage. Thus, according to the present invention, tissues that neighbor those singled out for photoablation are protected by loading the neighboring tissues with a quenching photodynamic agent that is not sought to be photosensitized.

The present inventor shows that competitive quenching can be achieved by using, for example, the perihydroxylated dianthraquinone, hypericin, to protect various cell types from photosensitization with the benzoporphyrin derivative verteporfin and argon laser at 689 nm. Using hypericin as a preferred example of a quenching photosensitizer molecule, the present invention is useful when hypericin is dispersed in the extravascular compartment of tissues sought to be protected, while verteporfin is sequestered in the vasculature of organs targeted for photoablation. One preferred embodiment of the present invention can be practiced in the treatment of pathological choroidal neovascularization associated with age related macular degeneration (AMD). Current therapy utilizes photodynamically-induced obliteration of pathological vessels by verteporfin confined to the intravascular compartment. However, leakage of verteporfin from the intravascular compartment triggers phototoxicity and apoptosis of adjacent retinal pigmented epithelial (RPE) cells, damaging neuronal photoreceptor cells and leading to blindness. The presence of hypericin in RPE cells resulting from practicing the present invention is shown to impart considerable protection from phototoxicity, even though it does not prevent verteporfin entry into RPE cells.

The present inventor has demonstrated in rats that conditions can be achieved in which hypericin disperses in the retina, while verteporfin is confined to the intravascular compartment. It is further shown by the present inventor in the Example presented hereinbelow that a high degree of protection from the phototoxicity of verteporfin and light can be generated in RPE or other epithelial cells by loading with hypericin as long as light with wavelengths of less than 650 nm, i.e., in the absorption range of hypericin, is avoided. This protective phenomenon is termed "competitive quenching" by the present inventor because hypericin does not appear to prevent verteporfin entry into RPE cells and only appears to counteract its light-mediated phototoxicity. "Competitive quenching" with hypericin according to the present invention can be used to protect retinal tissues from verteporfin-mediated phototoxicity as well as tissues neighboring tumors targeted for photo-elimination.

The present invention thus provides a general method for regulating the localized phototoxicity of an effector photosensitizer molecule during photodynamic therapy by quenching the activity of the effector photosensitizer molecule in neighboring tissues of the tissue targeted for destruction. The general method involves administering to a patient in need thereof, preferably by intravenous administration, a quenching photosensitizer molecule, the absorption spectrum of which falls outside the wavelength range used to excite the effector photosensitizer molecule, prior to administering the effector photosensitizer molecule to the patient and performing photodynamic therapy. Thus, by being present in the neighboring tissues of the tissue targeted for destruction during photodynamic therapy, the quenching photosensitizer molecule is capable of quenching photosensitization in case any effector photosensitizer molecules may have leaked into the neighboring tissues.

The tissue targeted for destruction according to the present invention may be any tissue that is accessible to light whether by direct laser beams or by fiber optics. It is preferably a light-accessible localized tumor or a pathological blood vessel emerging from the retinal choroid in the neovascular form of age related macular degeneration.

In a preferred embodiment of the present invention, the present method is directed to preventing or reducing the adverse effects to retinal pigmented epithelium during photodynamic therapy of age related macular degeneration with an effector photosensitizer molecule. A quenching photosensitizer molecule is administered, preferably intravenously, to a patient prior to administration of an effector photosensitizer molecule and prior to photodynamic therapy to prevent or reduce the formation of reactive oxygen species and the damage induced by the light-excited effector photosensitizer molecule in the retinal pigmented epithelium during photodynamic therapy. Currently, the benzoporphyrin derivative verteporfin is the sole effector photosensitizer molecule approved by the U.S. Food and Drug Administration (FDA) for use with an argon laser at 689 nm in photodynamic therapy of age related macular degeneration.

It will be appreciated by those of skill in the art that for other suitable effector photosensitizer molecules, such as those yet to be approved for use in photodynamic therapies by the FDA, a quenching photosensitizer molecule can be suitably selected by those in the art as they would be quite skilled in quenching the excitation of a photosensitizer molecule from a knowledge of how to quench fluorescence. Non-limiting examples of suitable effector photosensitizers include dianthraquinones, porphicenes, porphins, hypocrellins, etc.

The quenching photosensitizer molecule is a photodynamic agent the absorption spectrum of which falls outside the wavelength range used to excite the effector photosensitizer molecule for photodynamic therapy. Preferably, the quenching photosensitizer molecule is a dianthraquinone, and when verteporfin is the effector photosensitizer molecule, the quenching photosensitizer molecule is more preferably hypericin or dimethyl tetrahydroxy helianthrone (DTHe), and most preferably hypericin.

Hypericin, a perihydroxylated dianthraquinone has been selected to be the most preferred protective agent because of a unique combination of properties. Absorption spectra at 545 and 590 nm conveniently below the range of verteporfin, lipophilicity that attributes an alpha half-life in the range of about 1–2 hours in the circulation and prolonged tissue levels with an elimination half-life in the range of 48 hours in humans and moderately low red/ox potentials ($E_1/V=-1.01$ and $E_2/V=-1.31$) (Lavie et al., 1994). These red/ox properties enable hypericin to act as both electron acceptor and donor, facilitating energy scavenging from bioenergized electron transfer reactions in the cell and establishing the molecular platform for the biological activity of hypericin in the dark (Blank et al., 2001).

Molecules possessing lower red/ox potential are more likely to serve as acceptors, to compete with electron transfer and generation of free radicals, and to interfere with formation of superoxides and peroxides.

The quenching photosensitizer molecule is preferably administered intravenously in a range of about 2 to 72 hours prior to intravenous administration of the effector photosensitizer molecule for performing photodynamic therapy. Hypericin as the preferred quenching photosensitizer molecule is preferably administered intravenously at a dose in a range of about 0.01–2 mg/kg, more preferably in a range of about 0.01–0.5 mg/kg.

The aim is to achieve conditions in which the quenching photosensitizer extravasates from the blood into the tissues and completely clears from the vascular compartment including the vascular endothelium which lines the blood vessels. At the same time, the effector photosensitizer is freshly administered intravenously so as to be confined to the vascular compartment (in the retinal choroid) where photosensitization with light will result in ablation of the blood vessel containing the effector photosensitizer but not in tissue containing the quenching photosensitizer molecule.

A preferred embodiment of the method of the present invention which prevents or reduces the adverse effects, i.e., phototoxicity, to the retinal pigmented epithelium (RPE) during photodynamic therapy of age related macular degeneration is therefore also an improvement to the currently approved photodynamic therapy using verteporfin and an argon laser for treating age related macular degeneration because it overcomes the pitfalls of this therapy by avoiding phototoxicity damage to the RPE.

Also encompassed by the present invention is a method for preventing adverse effects to neighboring tissues during photodynamic occlusion of blood vessels by an effector photosensitizer molecule, where a quenching photosensitizer molecule that possesses a long tissue half-life and quenches the photodynamic activity of the effector photosensitizer molecule is administered to a patient to prevent or reduce the formation of reactive oxygen species during photodynamic therapy.

Having now generally described the invention, the same will be more readily understood through reference to the following example which is provided by way of illustration and is not intended to be limiting of the present invention.

EXAMPLE

Materials and Methods

Chemicals

Hypericin was synthesized by Dr. Y. Mazur, Dept. of Organic Chemistry, Weizmann Institute of Science, Israel, as described previously (Lavie et al., 1999; U.S. Pat. No. 5,120,412). The compound was dissolved in 70% aqueous ethanol to a stock solution of 2 mg/ml from which subsequent dilutions were made in sterile medium to obtain a final ethanol concentration <1%. Verteporfin was obtained from Nvartis Ophthalmics.

Cell Lines and Culture Conditions

ARPE-19 cells were obtained from the ATCC. The cells were maintained in a medium consisting of equal volumes of HAM F-12 and Dulbecco's MEM, 40 µM glutamine, 100 units/ml penicillin and 100 µg/ml streptomycin (GibcoBRL Life Technologies Ltd, Paisley, Scotland) supplemented with 10% fetal bovine serum (FBS) (ATCC). The cells were grown as monolayers in a controlled atmosphere (37° C., 5% $CO_2$).

Animals

Male Wistar rats 12–14 weeks of age were purchased from Harlan (Jerusalem, Israel). All experiments were approved by the Animal Care Committee of the Beilinson Medical Center and conducted in strict accord with the guidelines of the Israeli Ministry of Health. Prior to experimentation, the animals were anesthetized with ketamine xylazine and exanguinated by cervical dislocation.

Photosensitization of RPE and EH Cells With Verteporfin

ARPE or EH cells were plated in 96 well flat bottom microplates 2×10⁴ cells/well. The cells were allowed to attach to the plate surface and hypericin was added to the cultures in complete darkness (ambient light kept below <0.03 mW/cm² to prevent hypericin-mediated phototoxicity) for time intervals ranging from 3–6 hrs. Verteporfin was then added and was present for the last two hours of the incubation period. At the end of incubation period, the growth medium containing hypericin and verteporfin was removed and replaced with phosphate buffered saline (PBS) and then photosensitized with red light using a fiber-optic non-coherent light delivery system (SeNet Ltd, Israel) in combination with K700 broadband interference filter with central wavelengths at 700 nm and half-height bandwidth of ±40 nm (Rolyn Optics, Covina, Calif.) to selectively excite verteporfin but not hypericin (excitable at 546 and 590 nm). The cultures were then returned to standard growth medium, cultured for 24 hrs in a 37° C., 5% $CO_2$ and cell viability then assayed by the MTT or Hemacolor assays. The fluence rate (mW/cm²) was measured with a Model IL 1400A radiometer/photometer (International Light Inc., Newburyport, Mass.).

Cell Viability Analyses

Two methods have been used to monitor cell viability: the MTT assay which measures reduction of MTT to formasan by mitochondria of viable cells and by the Hemacolor assay, a calorimetric microtiter assay that quantifies the amount of dye that binds to viable adherent cells (Keisari, 1992). The cells were plated in flat-bottomed 96 well plates in 200 µl medium containing the photosensitizer. MTT was added to the cells following light irradiation and the plates were incubated for three hours and then analyzed in an ELISA reader at 560 nm. Corrections were made for non-specific absorption of MTT subtracting background values generated in cell free blank wells containing medium and HY at each dose level and MTT.

For the Hemacolor assay the cells were fixed with methanol, stained with Hemacolor reagents (Merck, Darmstadt, Germany), the dye eluted and quantified in an ELISA reader at 650 nm. PDT efficacy was expressed as percentage of viable cells in treated wells relative to untreated controls, calculated as $(OD_{650, treated}/OD_{650, untreated}) \times 100$.

Measurement of Intracellular Hypericin Accumulation

ARPE and EH cells were seeded into a 96-well flat-bottom microplate (Costar, Corning, N.Y.) at a concentration of 5×10⁴ cells/well. Twelve hours later, the supernatant was replaced with fresh DMEM containing different concentrations of hypericin and the plates were incubated for 3 hrs. Verteporfin (2–10 µg/ml) was then added for the last two hours of the incubation period. At the end of the incubation period, supernatant was discarded and the cells were washed twice with PBS containing 2% BSA and once with PBS. The cells were dissolved in 0.2 ml of 10% Triton-X in acidified isopropanol and subsequently diluted with 1.8 ml 70% ethanol. The fluorescence intensity of these homogeneous samples, containing verteporfin with/without hypericin taken up by the cells, was measured in triplicates with a spectrafluorophotometer (Shimadzu, model RF-5301PC), $\lambda_{exc}=690$ nm and $\lambda_{em}=699$ nm. Measurements were corrected for background signal of the solvents and compared to controls (cells) that represent light scattering.

Determination of Hypericin Distribution Among the Different Layers of the Retina Rats were sacrificed at 15 min, 2 hrs, 6 hrs and 8 hrs after i.v. administration of hypericin, 2 mg/kg. The eyes were enucleated and frozen initially at −80° C. and subsequently in liquid nitrogen and several cryostat sections (5-µm width) sliced from each sample. To prevent hypericin extraction from the retinal tissues during staining the histological tissue distribution of hypericin among the different layers of the retina was initially examined under an Olympus phase contrast and fluorescence microscope, and the data photographed with a computer-linked digital camera (Multipixel Spectral Imaging System, Applied Spectral Imaging Inc., Israel. Hypericin was excited at 477 nm and its fluorescence recorded by documenting emission intensity at 602 nm. The photographed locations were marked and the sections then stained with Hematoxylin-eosin (H&E) for confirmation of retinal layer identity and compared to the corresponding fluorescence and light microscopy images.

Results

Protection of ARPE Cells From Verteporfin-Induced Phototoxicity by Hypericin

Figure 2A:
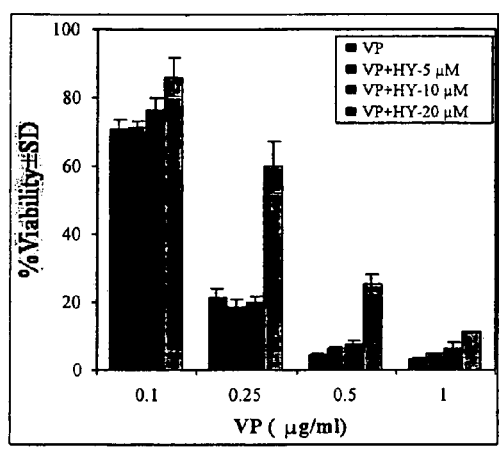
FIGS. 2A–2D show graphs of percent viability of ARPE cells treated with hypericin and verteporfin and photosensitized at >650 nm, the absorption spectrum of verteporfin.

In order to examine whether the red/ox properties of hypericin in the dark can impact on the phototoxic properties of verteporfin (VP), retinal pigmented epithelial cells (ARPE-19) in monolayer cultures were loaded with hypericin by exposure to 5, 10 and 20 µM of this compound for three and six hrs. Verteporfin at concentrations ranging between 0.1–1.0 µg/ml was administered to the cells for the last two hours of incubation in the dark. The cells were then washed with PBS, the medium replaced and the cultures exposed to 0.75 J/cm² of light irradiation at wavelengths >650 nm which coincide with the absorption spectrum of verteporfin but not with that of hypericin. Following irradiation, drug-free fresh medium was introduced, the cells incubated at 37° C. in a 5% $CO_2$ incubator for additional 24 hrs and cell viability then monitored using the MTT assay. FIG. 2A shows that verteporfin at concentrations of 0.25, 0.5 and 1 µg/ml elicited approximately 80%, 93% and 96% loss of cell viability, respectively. However, the presence of hypericin in the cells protected the cells and increased their survival substantially. When 0.25 µg/ml of verteporfin was used for photosensitization, the percent cell viability increased from 20% to 60% in the presence of hypericin administered as an 20 µM solution (approximately 10 µg/ml), and from 6% in cells treated with 0.5 µg/ml of verteporfin solution to 25% in the presence of 20 µM of hypericin (FIG. 2A).

Figure 2B:
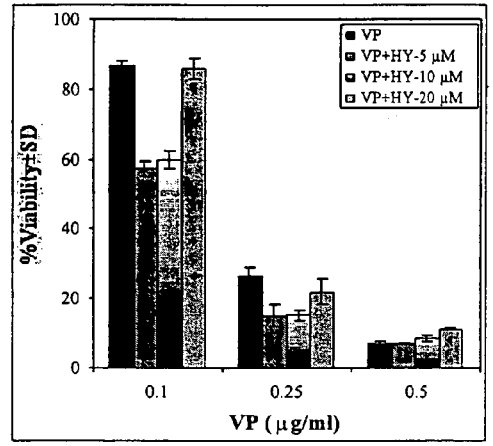
Figure 2C:
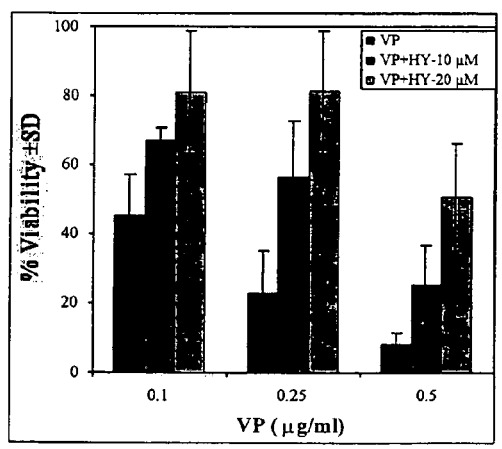
Figure 2D:
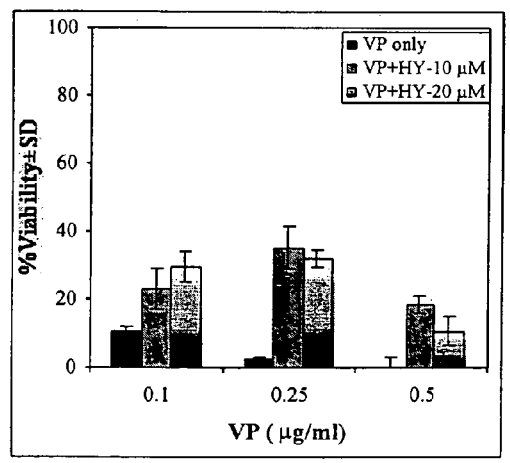

The duration of exposure to hypericin was also found to affect the level of cell protection from VP-mediated phototoxicity. Cell exposure to hypericin for 3 hrs prior to phosensitization was effectively protective against VP-induced phototoxicity; however, protraction of cell incubation with hypericin to 6 hrs resulted in loss of protection (FIG. 2B). Another factor that appears to affect competitive quenching is the dose of light. Competitive quenching protection by hypericin was highly effective following cell irradiation with 0.96 J/cm$^2$ (FIG. 2C). Following increase of the light dose to 1.73 J/cm$^2$ the relative protection by hypericin was maintained, however, the absolute levels of protection marked by percent cell viability has declined (FIG. 2D).

Figure 3A:
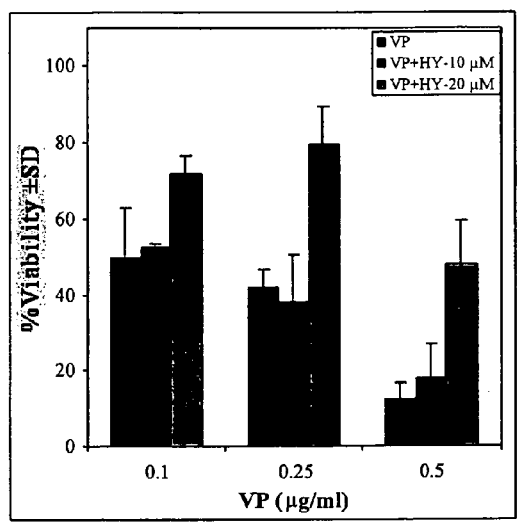
FIGS. 3A and 3B show EH endothelial cells treated with hypericin and verteporfin and exposed to 0.96 J/cm$^2$ (FIG. 3A) or 1.73 J/cm$^2$ (FIG. 3B) of light irradiation at >650 nm.
Figure 3B:
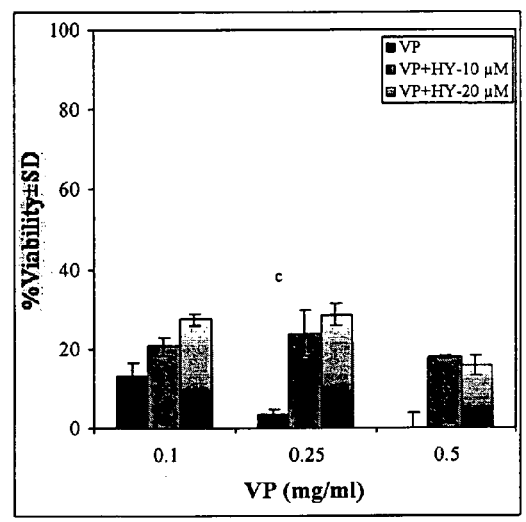

The protection of RPE cells from VP-mediated phototoxicity by hypericin prompted examination of the effects of hypericin on VP-mediated phototoxicity in endothelial cells. EH cells were used for this purpose. FIGS. 3A and 3B shows that hypericin also protected EH cells from phototoxicity induced by VP. EH cell viability following phototoxicity elicited by 0.1 μg/ml of verteporfin and 0.96 J/cm$^2$ of light increased from 50% in the absence of hypericin to 73% in the presence of 20 μM of this compound, following photosensitization with 0.25 μg/ml of verteporfin from 42% in the absence of hypericin to 81% viability in the presence of 20 μM of this compound and in the presence of 0.5 μg/ml of verteporfin from 12% in the control to 49% in the group treated with 20 μM of hypericin (FIG. 3A). Similar to RPE cells, relative EH cell protection by hypericin from verteporfin-induced phototoxicity was also maintained at higher doses of light irradiation, yet the absolute levels of protection declined (FIG. 3B).

Effect of Hypericin on the Intracellular Accumulation of VP in ARPE or EH Cells

The protection of ARPE and endothelial cells by hypericin from VP-mediated phototoxicity following photosensitization with light across a 650–700 nm cutoff filter prompted examination of whether protection is a result of interference with VP cell entry by hypericin. To examine this question ARPE cells were seeded 5×10$^4$ cells/well in 96 well flat bottom microplates. The cells were allowed to adhere overnight after which time hypericin at concentrations 2 μg/ml; 5 μg/ml, 10 μg/ml and 20 μg/ml was added and the cells incubated for one hour at 37° C. VP at concentrations 2 μg/ml, 5 μg/ml and 10 μg/ml was then applied to the cultures for additional two hours. The supernatants were removed and the cells wash twice with 0.5% BSA in PBS. The cells were lysed in 200 μl 0.04 N HCL in acidified isopropanol and the mix transferred into cuvettes containing 1.8 ml 70% Ethanol and VP fluorescence measured at 699.1 nm in a RF05301 PC spectrofluorometer (Shimadzu, Japan) following excitation at 690 nm. Percent VP concentration was determined in HY pre-treated versus untreated samples.

Figure 4A:
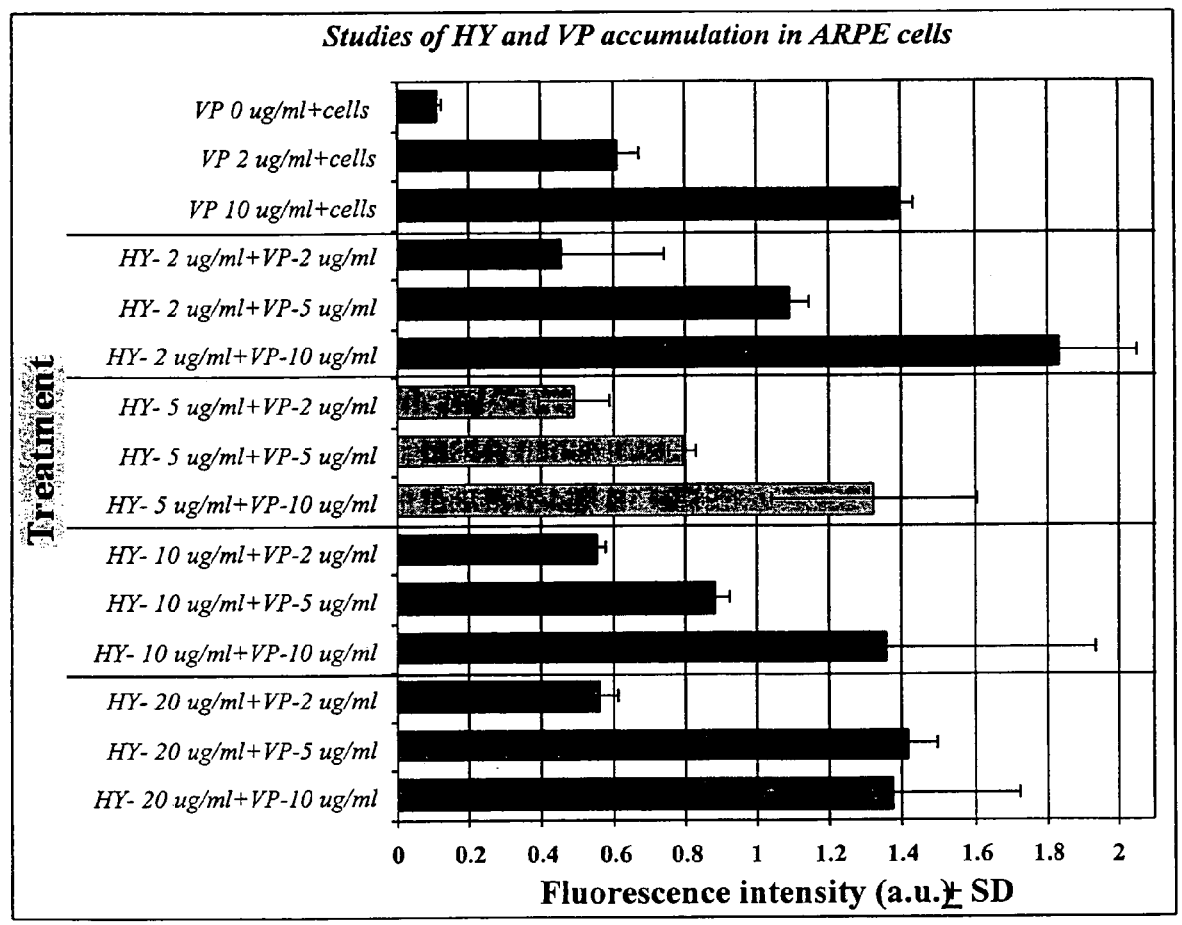
FIGS. 4A and 4B show the effect of hypericin on accumulation of verteporfin in human ARPE cells (FIG. 4A) and human endothelial EH cells (FIG. 4B) as measured by fluorescence intensity.
Figure 4B:
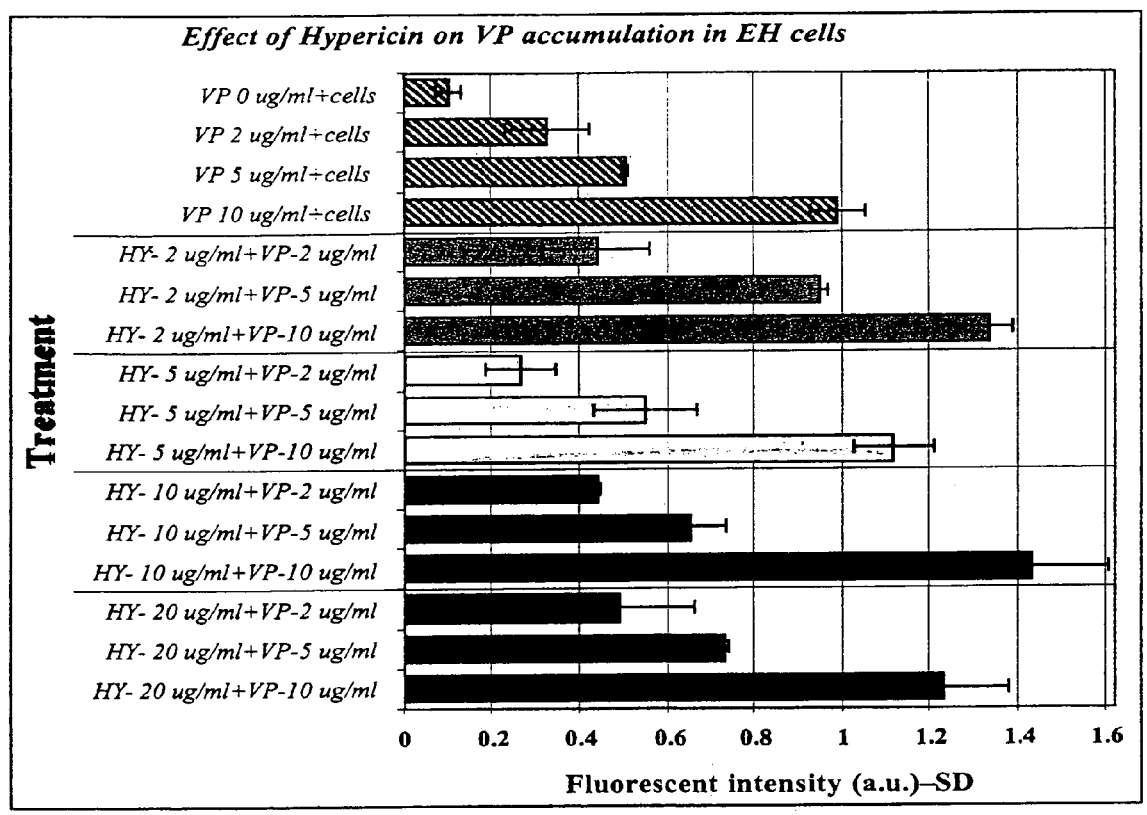

The results, shown in FIGS. 4A and 4B, indicate that verteporfin accumulation within RPE cells was unaffected by the presence of hypericin in the cultures (FIG. 4A). Similarly, accumulation of verteporfin in endothelial cells was also unperturbed by hypericin at all concentrations examined (FIG. 4B). Thus, protection of both cell lines by hypericin from verteporfin-induced phototoxicity was unexpectedly not the result of verteporfin displacement or prevention of entry into the cells by hypericin.

Selective Protection of Neighboring Tissues From Collateral Phototoxic Damage During Photosensitization of Tissues Targeted for Ablation In the neovascular form of age related macular degeneration, photodynamic occlusion of the pathological microvessels that emerge from the choroid is sought in order to prevent macular vision loss. At the same time the RPE must be protected from phototoxicity that might occur from any leakage of the intravascularly-confined verteporfin photosensitizer. Since hypericin was noted to protect both RPE as well as endothelial cells from phototoxicity via "competitive quenching", its use might diminish the photodynamic damage required for the occlusion and ablation of the pathological microvessels and interfere with the efficacy of the treatment.

Figure 5:
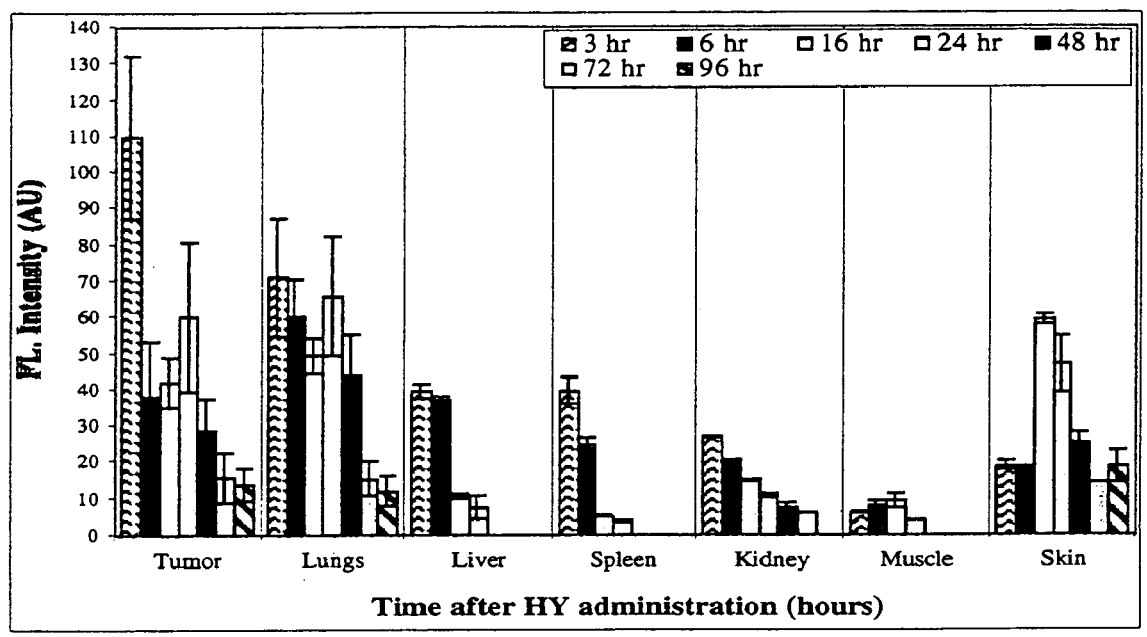
FIG. 5 shows the biodistribution of hypericin in various tissues of BALB/c mice bearing breast adenocarcinoma tumors in their skin as measured by fluorescence intensity over time after hypericin administration.

The present inventor aimed to overcome this obstacle by using pharmacokinetic considerations. Hypericin is a lipophilic agent with an alpha half life of approximately 1–2 hours in the circulation. The compound then extravasates and accumulates in the tissues with a gamma elimination half life of approximately 48 hrs from tissues. It is therefore possible to generate conditions in which hypericin has cleared from the circulation and concentrated in the tissues where it can be useful in protecting from collateral photodynamic damage. Preliminary pharmokinetic properties of hypericin in mice are shown in FIG. 5, where hypericin was found to sequester in various tissues for many hours.

Figure 6A:
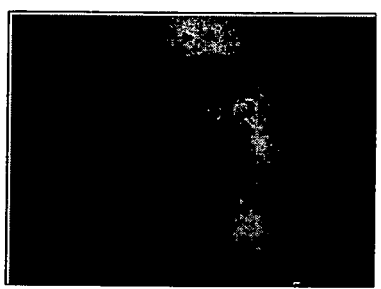
FIGS. 6A, 6B and 6C are images of hypericin fluorescence in sections of rat retina at 15 min., 2 hrs, and 6 hrs after hypericin administration, and FIGS. 6D, 6E, and 6F correspond to light microscopy images of the same sections as shown respectively in FIGS. 6A, 6B, and 6C.
Figure 6B:
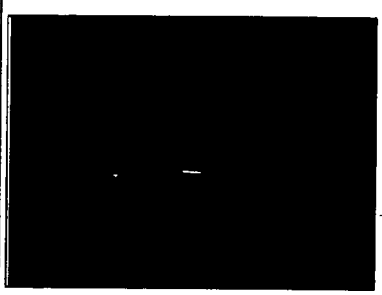
Figure 6C:
Figure 6D:
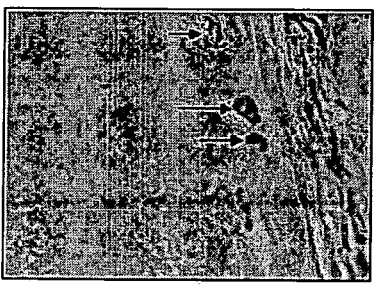
Figure 6E:
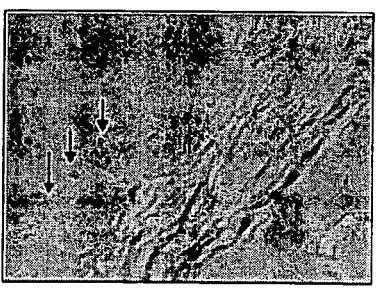
Figure 6F:
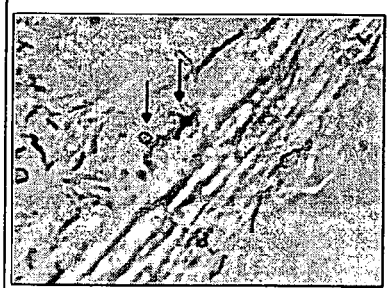

The present inventor has undertaken to examine in rats whether intravenously administered hypericin is bioavailable to the retina and to delineate the retinal layers in which it accumulates. Hypericin at a dose of 2 mg/kg was administered to the tail vein. At 15 minutes, 2, 4, 6 and 8 hrs the rats were anesthesized, the eyes enucleated and frozen sections prepared. The sections were then analyzed by Multipixel Spectral Imaging. The results show that hypericin is bioavailable to the retina. At 15 minutes, the compound was confined mainly to the vasculature and hypericin fluorescence was detected predominantly within or in association with choroidal blood vessels (FIG. 6A). Two hrs after administration, hypericin extravasated to the surrounding tissue was less evident within the vasculature and spread through the choroid (FIG. 6B). At 6 hrs, the compound spread to the entire retina (FIG. 6C). These observations demonstrate that hypericin can be useful in protecting different retinal layers from verteporfin mediated cytotoxicity.

Figure 1B:
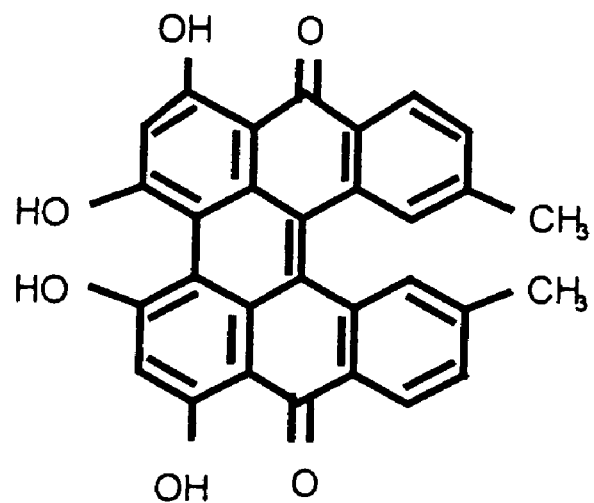
FIG. 1B shows the chemical structure of dimethyl tetrahydroxy helianthrone.
Figure 7A:
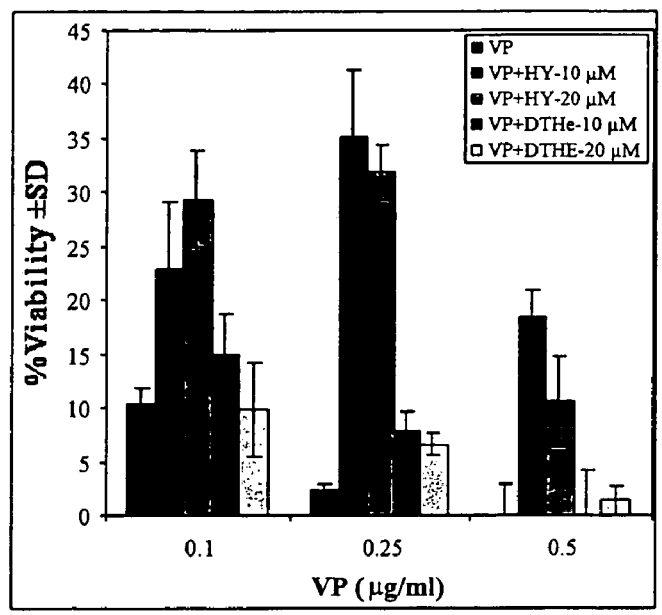
FIGS. 7A and 7B show a comparison of the efficacy of competitive quenching between the dianthraquinones, hypericin and dimethyltetrahydroxy helianthrone (DTHe), in ARPE cells (FIG. 7A) and in vascular endothelial EH cells (FIG. 7B). The cells were treated with the added dianthraquinone compounds for 3 hrs. and with added verteporfin for the last two hrs. The cells were then exposed to 1.73 J/cm$^2$ of light irradiation at >650 nm and cell viability monitored after 24 hrs. in culture.
Figure 7B:
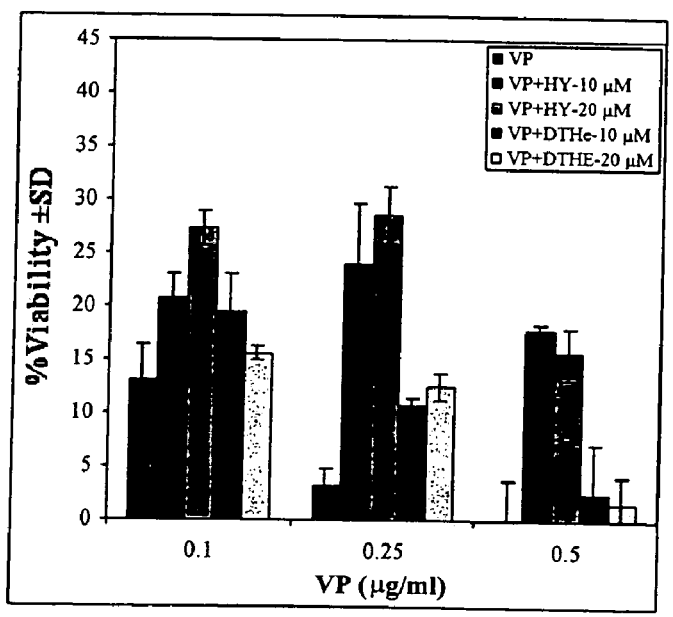

Structure-Activity Relationships in Competitive Quenching: Protection by Other Dianthraquinones Structurally Related to Hypericin In order to examine the universality of the "competitive quenching" phenomenon and to obtain better understanding of the structural requirements for obtaining optimal quenching of effector photosensitizer activity, the present inventor investigated quenching of verteporfin phototoxicity by dimethyl tetrahydroxyhelianthrone (DTHe) (FIG. 1B), a structural analog of hypericin. ARPE or EH endothelial hybridoma cells were seeded at 5×10$^4$ cells/well in 96 well flat bottom microplates. The cells were allowed to adhere overnight, after which time DTHe or hypericin were added to ARPE cells (FIG. 7A) or to endothelial hybridoma cells (FIG. 7B) at concentrations of 10 or 20 μg/ml and the cells incubated at 37° C. in complete darkness. After one hour incubation with hypericin, verteporfin at concentrations of 0.1, 0.25 and 0.5 μg/ml was added to the cultures, which were then incubated at 37° C. for two additional hours. The supernatants were removed, the cells washed with PBS and the cultures exposed to light irradiation at a dose of 1.73 J/cm$^2$ at 689 nm. The cultures were then incubated at 37° C. for an additional 24 hrs and cell viability was then determined via the hemacolor assay. The results show that in ARPE cells photosensitized with 0.25 μg/ml of verteporfin cell viability increased from 3% in cells not protected by competing quenchers to 35% and 32% when hypericin at concentrations of 10 and 20 μg/ml, respectively, was added to the cultures. Addition of DTHe as the quenching photosensitizer at concentrations of 10 and 20 µg/ml increased cell viability only to 7.5 and 6%, respectively. These results indicate that while DTHe did exhibit competitive quenching activity, it was much less effective as a "competitive quencher" (quenching photosensitizer) of verteporfin-mediated phototoxicity than hypericin.

Discussion

Photodynamic therapy relies on inducing photo-oxidative damage that destroys a selected target tissue, be it a tumor and its supplying microvasculature or a pathological blood vessel in the retina. Inability to accurately limit the photosensitized fields to the desired targets leads to a major drawback of this treatment—phototoxicity to adjacent tissues. Since in the case of choroidal neovascularization (CNV) this can translate into irreversible blindness, development of methods that confine the phototoxic damage to the targets and protect juxtaposed tissues, is needed.

A unique combination of photochemical and lipophilic properties render the perihydroxylated naphthodianthrone, hypericin, useful in performing this task via a novel approach described here by the present inventor. It constitutes a protective phenomenon in which hypericin protects cells from phototoxicity by other light-activated photosensitizers, such as verteporfin. The phenomenon has been termed "Competitive Quenching" because hypericin does not appear to prevent verteporfin entry into RPE cells and only counteracts its light mediated phototoxicity. The present inventor could not detect any physico-chemical interactions between hypericin and verteporfin in cells as the light absorption and fluorescence properties that are unique to each of these two compounds were unaffected. Hypericin appears to quench the formation of reactive oxygen species by the photoactivation of verteporfin. This explanation is most feasible since direct excitation-energy transfer from verteporfin to hypericin seems unlikely because light absorption by hypericin occurs at wavelengths that are significantly shorter than the absorption range of verteporfin.

Here, the feasibility of this approach in preventing phototoxicity is demonstrated in vitro and the in vivo pharmacokinetic requirements for its utilisation in protecting the retinal pigmented epithelium from verteporfin-induced phototoxicity during PDT of CNV are defined. Effective hypericin dose-dependent protection of cell viability from verteporfin-induced phototoxicity was performed achieved in RPE or endothelial cells by loading with hypericin prior to the activation with light. Cell viability was preserved at levels of up to 40.5% when photosensitization was performed with 0.5 µg/ml of verteporfin (FIG. 3A) and at levels of up to 46.8% with 2 µg/ml of verteporfin when hypericin was introduced into the cells prior to photosensitization of verteporfin. For reasons that are not yet fully understood, cell viability protection by hypericin was highly effective at the first three hours following hypericin administration to the cells and efficacy appears to have diminished by 6 hrs.

Hypericin is particularly suitable for the competitive quenching of verteporfin mediated photosensitization because of the large differences in wavelength absorption between hypericin excited at 545 and 589 nm and verteporfin, which is excited at 689 nm. This facilitates preventing the excitation of the quenching photosensitizer, hypericin by using filters with a cutoff $\geq 650$, as the latter molecule is itself a powerful photosensitizer.

Most intravenously administered drugs spread over time from the intravascular compartment to adjacent tissues, enabling utilization of the temporary blood-tissue barrier in order to establish high tissue levels of the quenching photosensitizer against high intravascular concentration of the photoactivated sensitizer. In the case of hypericin, this was achieved 2 hours after intravenous administration to rats. In the retina, hypericin was mainly confined to the choroidal vasculature for up to one hour and beyond 2 hrs was cleared from the choroidal vessels and accumulated in the extravascular choroid and RPE. A secondary intravenous administration of verteporfin at this time can create two separate compartments with verteporfin in the vascular compartment and hypericin in the tissue. Irradiation with light $\geq 650$ nm at this stage is believed to cause occlusion and ablation of the pathological vessel in CNV with no interference from hypericin, the competitive quenching of which will be confined to the adjacent retinal pigmented epithelium.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Agostinis et al. (1995) Photosensitized inhibition of growth factor-regulated protein kinases by hypericin. *Biochem. Pharmacol.* 49:1615–1622

Blank et al. (2001) Anti-cancer activities of hypericin in the dark. *Photochem. Photobiol.* 74:120–125.
Brown et al. (2001) Verteporfin: a milestone in opthalmology and photodynamic therapy. *Expert Opin. Pharmacother.* 2:351–61.
Degar et al. (1991) In: HIV Disease: Pathogenesis and Therapy, University of Miami, abstract No. 1–16
Dougherty (1983) Hematoporphyrin as a photosensitizer of tumors. *Photochem. & Photobiol* 38:377–379
Duran et al. (1986) *Photochem. Photobiol.* 43:677–689
Giese, (1980) *Photochem. Photobiol. Rev.* 5:229–255
Keisari (1992) A colorimetric microtiter assay for the quantitation of cytokine activity on adherent cells in tissue culture. *J. Immunol. Methods* 146, 155–161
Lavie et al. (1990) *Ann. New York Acad. Sci. USA* 616: 556–562
Lavie et al. (1989) Fifth Int'l Conf. on AIDS, Montreal, abstract C.501
Lavie et al. (1989) *Proc. Natl. Acad. Sci. USA* 86:5963–5967
Lavie et al. (1994) The chemical and biological properties of hypericin—A compound with a broad spectrum of biological activities. *Medicinal Res. Rev.* 15:111–119
Lavie et al. (1991) In: HIV Disease: Pathogenesis and Therapy, University of Miami, abstract 1∝27
Lavie et al. (1999) A photodynamic pathway to apoptosis and necrosis induced by dimethyl tetrahydroxy helianthrone and hypericin in leukemic cells. Possible relevance to photodynamic therapy. *Brit. J. Cancer.* 79:423–432
McCaughan (1984) Photoradiation of malignant tumors presensitized with hematoporphyrin derivative. *Progress in Clin. & Biol. Res* 170:805–827
McLeod et al. (2002) Quantifying Changes in RPE and Choroidal Vasculature in Eyes with Age-Related Mascular Degeneration. *Invest Ophthalmol Vis Sci* 43:1986–93
Meruelo et al. (1988) *Proc. Natl. Acad. Sci. USA* 85:5230–5234
Meruelo et al. (1991) In: HIV Disease: Pathogenesis and Therapy, University of Miami, abstract 1–291
Meruelo et al. (1992) Mode of action of hypericin as an antiretroviral agent and other relevant findings. In: *Natural Products As Antiviral Agents.* Eds. C. K. Chu and H. Cutler, Plenum Press, New-York pp. 91–119
Michels et al. (2002) Changes in neovascular membranes and normal choroid blood vessels after multiple photodynamic therapy treatments. *Ophthalmologe* 99:96–100.
Ochsner, (1997) Photophysical and photobiological processes in the photodynamic therapy of tumours. *J. Photochem. Photobiol. B* 39:1–18.
Schmidt-Erfurth et al. (1999) Photodynamic therapy with verteporfin for choroidal neovascularization caused by age-related macular degeneration: results of retreatments in a phase 1 and 2 study. *Arch. Ophthalmol.* 117:1177–1187.
Takahashi et al. (1989) Hypericin and pseudohypericin specifically inhibit protein kinase C: possible relation to their antiretroviral activity. *Biochem. Biophys. Res. Commun.* 165:1207–1212
Valentine et al. (1989) Fifth Int'l Conf. on AIDS, Montreal, abstract M. C. P. 18
Weiner et al. (1989) Fifth Int'l Conf. on AIDS, Montreal, abstract C-608.

What is claimed is:

1. A method for regulating the localized phototoxicity of an effector photosensitizer molecule during photodynamic therapy by quenching the activity of the effector photosensitizer molecule in neighboring tissues of the tissue targeted for destruction by photodynamic therapy, comprising administering to a patient in need thereof a quenching photosensitizer molecule, the absorption spectrum of which falls below the wavelength range used to excite the effector photosensitizer molecule so that the quenching photosensitizer molecule itself is not excited, prior to administering the effector photosensitizer molecule and performing photodynamic therapy to regulate the localized phototoxicity of the effector photosensitizer.

2. The method of claim 1, wherein the tissue targeted for destruction is a light-accessible localized tumor.

3. The method of claim 1, wherein the tissue targeted for destruction is a pathological blood vessel emerging from the retinal choroid in the neovascular form of age related macular degeneration.

4. The method of claim 3 which inhibits or reduces the adverse effects to retinal pigmented epithelium during photodynamic therapy of age related macular degeneration with the effector photosensitizer molecule by inhibiting or reducing the formation of reactive oxygen species and the damage induced by the light-excited effector photosensitizer molecule in the retinal epithelium during photodynamic therapy.

5. The method of claim 3, wherein the quenching photosensitizer molecule is a dianthraquinone.

6. The method of claim 3, wherein the quenching photosensitizer molecule is hypericin.

7. The method of claim 6, wherein the quenching photosensitizer molecule hypericin is administered intravenously at a dose in a range of about 0.01–2 mg/kg.

8. The method of claim 6, wherein the quenching photosensitizer molecule is administered intravenously at a dose in a range of about 0.01–0.5 mg/kg.

9. The method of claim 3, wherein the quenching photosensitizer molecule is administered intravenously in a range of about 2 to 72 hours prior to intravenous administration of the effector photosensitizer molecule for photodynamic therapy.

10. The method of claim 9, wherein the quenching photosensitizer molecule is a dianthraquinone.

11. The method of claim 9, wherein the quenching photosensitizer molecule is hypericin.

12. The method of claim 3, wherein the effector photosensitizer molecule is verteporf in.

13. A method for inhibiting adverse effects to neighboring tissues during photodynamic occlusion of blood vessels by an effector photosensitizer molecule, comprising administering to a patient in need thereof a quenching photosensitizer molecule that possesses a long tissue half-life and quenches the photodynamic activity of the effector photosensitizer molecule to inhibit or reduce the formation of reactive oxygen species in neighboring tissues during photodynamic therapy.

14. The method of claim 12, wherein the quenching photosensitizer molecule is a dianthraquinone.

15. The method of claim 14, wherein the dianthraquinone is a perihydroxylated dianthraquinone.

16. The method of claim 15, wherein the perihydroxylated dianthraquinone is hypericin.

17. The method of claim 14, wherein the dianthraquinone is dimethyl tetrahydroxyhelianthrone (DTHe).

18. The method of claim 5, wherein the dianthraquinone is a perihydroxylated dianthraquinone.

19. The method of claim 3, wherein the effector photosensitizer molecule is a benzoporphyrin.

* * * * *